United States Patent [19]
Lisowsky

[11] Patent Number: 5,856,541
[45] Date of Patent: Jan. 5, 1999

[54] PROCESS FOR PREPARING 1 3-DISUBSTITUTED CYCLOPENTADIENYL LIGANDS AND TRANSITION METAL COMPLEXES THEREOF

[75] Inventor: Richard Lisowsky, Kamen, Germany

[73] Assignee: Witco GmbH, Bergkamen, Germany

[21] Appl. No.: 589,778

[22] Filed: Jan. 22, 1996

[30] Foreign Application Priority Data

Feb. 17, 1995 [EP] European Pat. Off. ........... 95102196.3

[51] Int. Cl.⁶ ..................................................... C07F 19/00
[52] U.S. Cl. ................. 556/43; 556/53; 556/58; 556/140; 585/350; 585/379
[58] Field of Search ................. 556/43, 53, 58, 556/140; 585/350, 379

[56] References Cited

U.S. PATENT DOCUMENTS 3,907,896  9/1975  Calame et al. ...................... 260/586 C
4,874,880  10/1989  Miya et al. ................................ 556/53

FOREIGN PATENT DOCUMENTS 128 045    6/1984   European Pat. Off. .
283 739    2/1988   European Pat. Off. .
366 290    10/1989  European Pat. Off. .
582 480    8/1993   European Pat. Off. .
2 313 504  5/1973   Germany .

OTHER PUBLICATIONS

Acheson et al. (1952) *J. Chem. Soc.*, 1127–1131.
McLean et al. (1965) *Tetrahedron, 21*:2313–2327.
Conta et al. (1970) Bull. Soc. Chiem., No. 8–9, 2981–2991.
Ellison (1972) *Synthesis*397.
(1976) *Chem. Ber., 109*: 329.
Houben–Weyl, vol. XIII/2a "Metallorganische Vergindungen Be, Mg, Ca, Zn, Cd", p. 47, Organomagnesiumsbergindugen–Georg Thieme Verlag Stuttgart, 1973.
Cadin et al. "Chemistry of oranozirconium and–hafnium compounds", Ellis Horwood Limited (1986).
Wailes et al. "Organometallic Chemistry of Titanium, zirconium, and Hafnium", Academic Press New York and London (1974).
Gmelin, *Handbuch der anorganischen chemie*, Supplement to 8th edition, vol. 10 and 11, "Zirconiumund Hafnium organische Vervindugen", p. 26ff, Verlag Chemie Weinheim (1973).
(1991) *J. Organomet. Chem.*, 417:9–27.

*Primary Examiner*—Amelia Owens
*Attorney, Agent, or Firm*—Scully, Scott, Murphy & Presser

[57] ABSTRACT

The invention relates to an improved process which, starting from 2-cyclopenten-1-ones substituted in the 3-position, gives a high yields of 1,3-dialkylcyclopentadienes which can be directly metallated and reacted to give the corresponding 1,3-dialkylcyclopentadienyl-transition metal complexes.

11 Claims, 3 Drawing Sheets

PROCESS FOR PREPARING 1 3-DISUBSTITUTED CYCLOPENTADIENYL LIGANDS AND TRANSITION METAL COMPLEXES THEREOF

FIELD OF THE INVENTION

The invention relates to an improved process which, starting from 2-cyclopenten-1-ones substituted in the 3 position, gives high yields of 1,3-dialkylcyclopentadienes which can be directly metallated and converted into the corresponding 1,3-dialkylcyclopentadienyl-transition metal complexes.

BACKGROUND OF THE INVENTION

Owing to the wide variety of possible uses of the above-mentioned transition metal complexes as catalysts in organic synthesis and, in particular, in the polymerization of olefins, the efficient industrial preparability of sandwich complexes which are disubstituted on the cyclopentadienyl radicals has become increasingly important (EP-A-O 128 045, EP-A-O 366 290, EP-A-O 283 739, EP-O 582 480, U.S. Pat. No. 4,874,880).

The preparation of such compounds is known in principle. The procedure according to equation (1) can generally be used for this purpose,

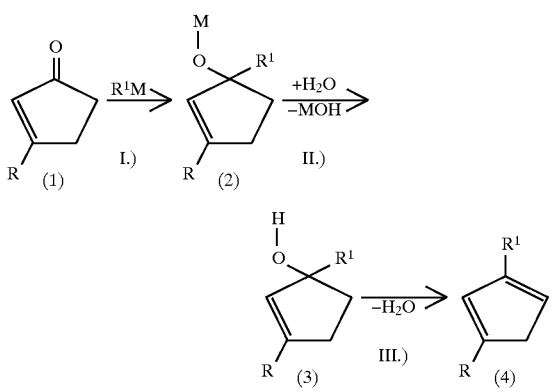

where

M can be Li, MgCl or MgBr;

R and $R^1$ are identical or different and each is an alkyl or aryl radical.

A disadvantage of this procedure was that after the reaction of 3-alkylcyclopenten-1-ones with Grignard compounds or lithium alkyls, the resulting alkoxide (2) first had to be hydrolyzed by means of water and isolated as alcohol (3) before, upon separate catalytic dehydration and work-up, the desired 1,3-dialkylcyclopentadiene component (4) was then obtained, and compound (3) could only be used for the further reaction after separate drying (Tetrahedron 1965, 21, 2313; Chem. Ber. 1976, 109, 329; J. Organomet. Chem., 1991, 417, 9).

It was therefore an object of the invention to simplify the reactions I., II. and III. (equation (1)) to such a degree as to provide a process which allows, in one reaction without isolation of the intermediates, the synthesis in high yields of 1,3-disubstituted cyclopentadienes which can then be reacted to give the corresponding transition metal complexes, e.g. according to equation (2):

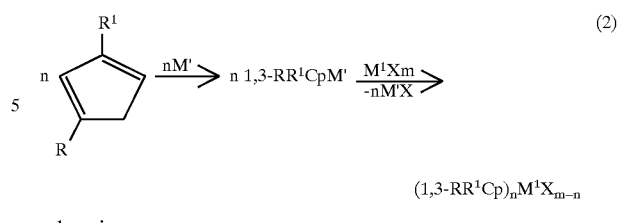

wherein

Cp denotes cyclopentadienyl;

M' is a metallating agent;

$M^1$ is a transition metal;

X is Cl, Br or I;

m is the oxidation state of $M^1$; and $n \leq m$.

BRIEF SUMMARY OF THE INVENTION

It has now suprisingly been found that the above reaction (equation (1)) for preparing 1,3-dialkylcyclopentadienes can allow, particularly when using Grignard compounds, the formation of the alcohol and the dehydration step III.) in an advantageous manner in situ without isolation of intermediates.

Furthermore, the magnesium salt thus formed simultaneously acts as desiccant and thus allows the immediate use of the solution obtained for preparing 1,3-dialkylcyclopentadienyl-transition metal complexes, since, owing to the solution of 1,3-dialkylcyclopentadiene being formed in anhydrous form, the latter can be treated immediately with moisture-sensitive metallating agents (such as Na, NaH, Li alkyls), converted into $1,3-RR^1CpM'$ and then reacted by conventional methods with transition metal salts. The overall scheme is shown in equation (3):

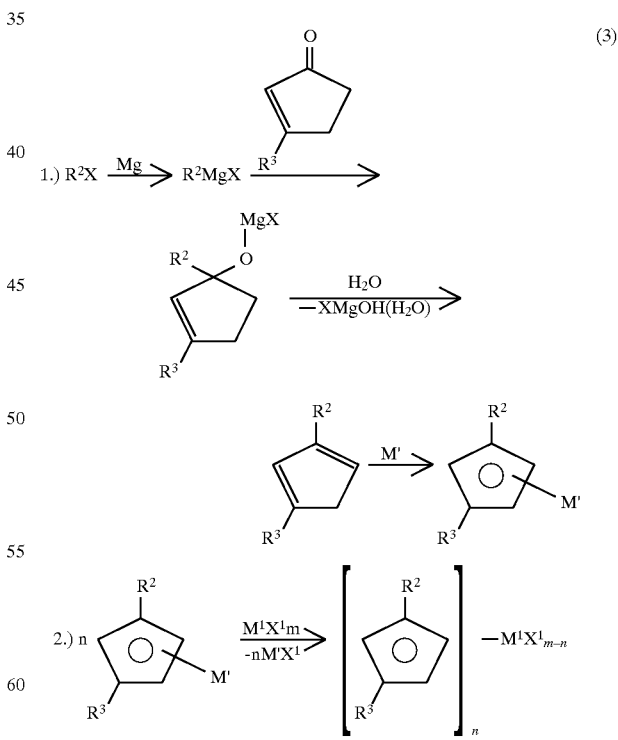

wherein each of $R^2$ and $R^3$ is independently of one another selected from the group consisting of $C_1-C_{20}$ substituted and unsubstituted, alkyl, alkenyl, cycloalkyl, aryl and arylalkyl radicals;

X is Cl, Br or I;

M' is a metallating agent such as Li, Na, K, NaH, KH, or Li alkyl;

$M^1$ is a transition metal such as Sc, Ti, Zr, Hf, Fe, V or Cr;

$X^1$ is Cl, Br or I;

m is the oxidation state of $M^1$; and n ≤ m.

The reaction procedure of the invention according to equation (3) is not possible for the processes of the prior art, since the alcohol prepared according to equation (1), stage II, first has to be isolated and subsequently separately dehydrated according to equation (1), stage III, and the water liberated in this reaction has to be completely removed before the further reaction according to equation (2) can be carried out to give the transition metal complexes.

The invention in one aspect provides a process for preparing 1,3-disubstituted cyclopentadienyl compounds which is characterized in that one or more cyclopent-2-en-1-ones substituted in the 3-position are reacted with one or more Grignard compounds according to equation (A)

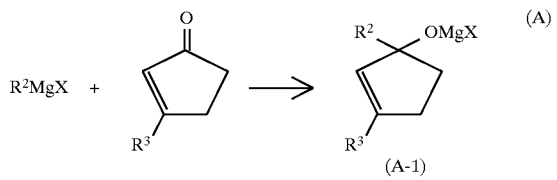

and the alkoxides (A-1) are hydrolyzed with no more than a stoichiometric amount of water and dehydrated in a step according to equation (B)

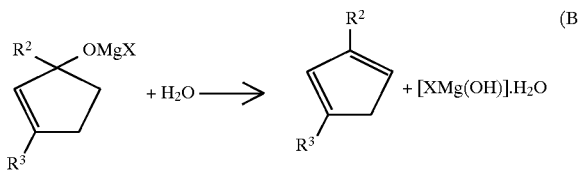

wherein each of $R^2$ and $R^3$, independently of one another is selected from the group consisting of $C_1$ to $C_{20}$, substituted and unsubstituted alkyl, alkenyl, cycloalkyl, aryl and arylalkyl radicals; and X is Cl, Br or I.

The invention in another aspect provides a process for preparing 1,3-disubstituted cyclopentadienyl-transition metal complexes, which is characterized in that the foregoing reactions (A) and (B) are carried out as a first step and, in a second step, the cyclopentadienyl product formed in equation (B) is directly metallated by methods known per se according to equation (C)

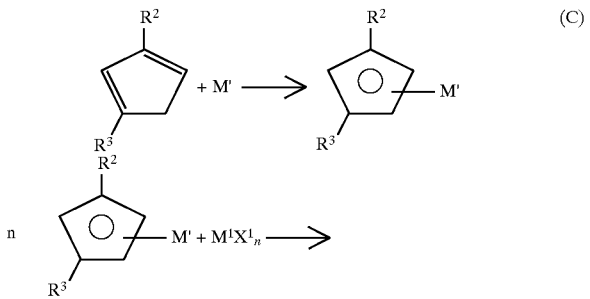

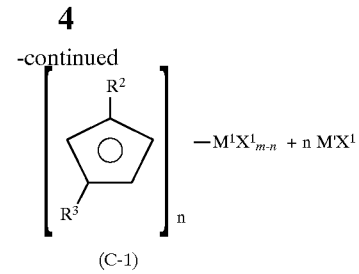

wherein

M' is a metallating agent;

$M^1$ is a transition metal such as Sc, Ti, Zr, Fe, V or Cr;

$X^1$ is Cl, Br or I;

m is the oxidation state of $M^1$; and n ≤ is m;

and the product (C-1) is reacted with one or more transition metal halides to give the corresponding complexes.

Further subject matter of the invention is characterized by the claims.

DETAILED DESCRIPTION OF THE INVENTION

Figure 1:
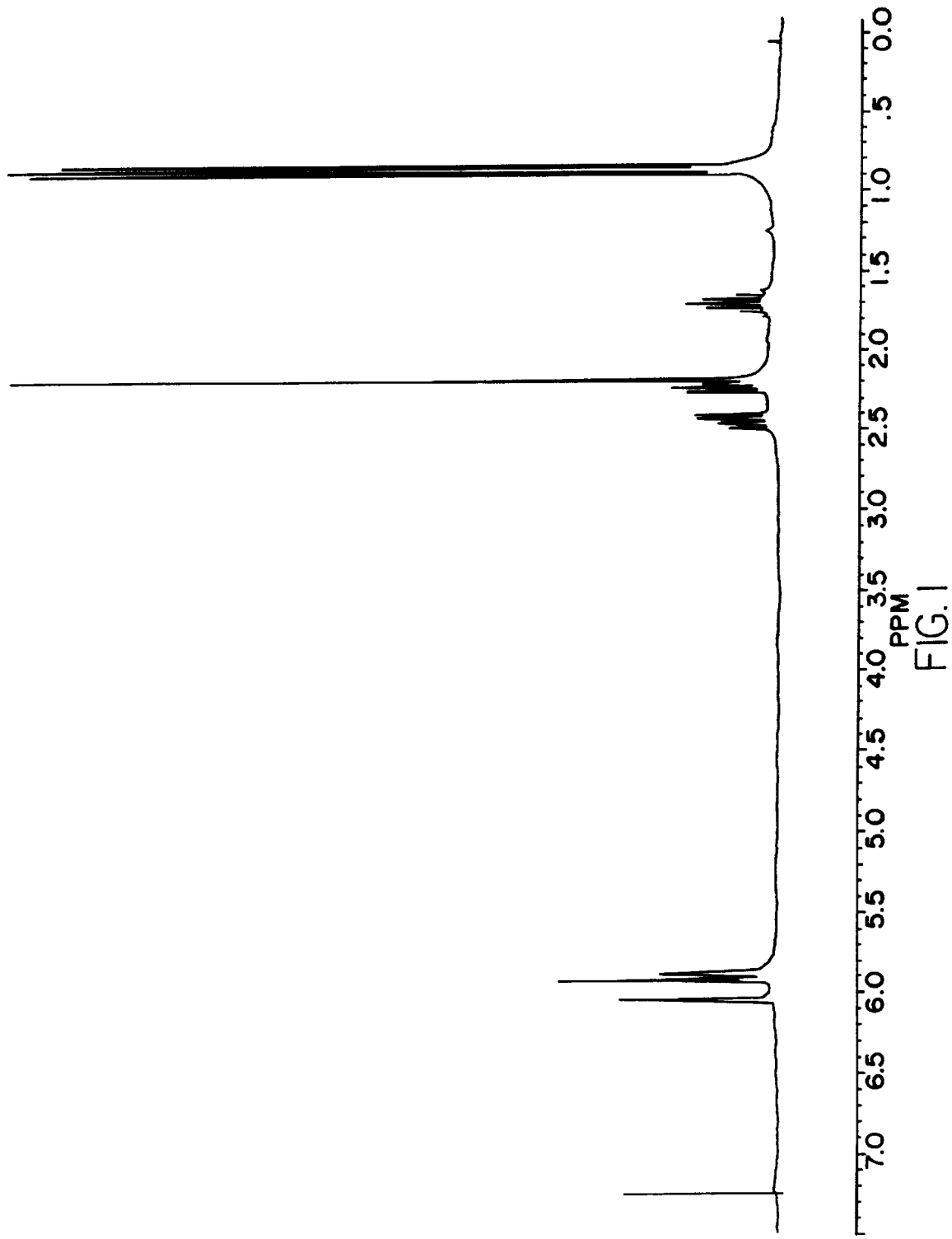
FIGS. 1–3 are nuclear magnetic resonance (NMR) spectra of products formed as described in Examples 2, 3(b), and 4, respectively.

The Grignard compounds $R^2MgX$ used according to equation (A) are commercial products or can be prepared by the generally known methods by reaction of the corresponding organochlorine, organobromine or organoiodine compounds with metallic magnesium as described, for example, in Houben-Weyl, Volume XIII/2a-Metallorganische Verbindungen Be, Mg, Ca, Sr, Ba, Zn, Cd; p. 47-Organomagnesiumverbindugen-Georg Thieme Verlag Stuttgart-1973.

Preference is given to using Grignard compounds $R^2MgX$ in which $R^2$ is a substituted or unsubstituted alkyl radical or cycloalkyl radical having 1–20 carbon atoms and X is as defined herein. Preferably, $R^2$ is n-butyl, i-butyl (isobutyl), or n-octyl.

The cyclopent-2-en-1-ones substituted in the 3-position which are used according to the invention can be prepared by literature methods (J. Chem. Soc., 1952, 1127; German Laid-Open Application 23 13 504; Tetrahedron Lett., 1965, 21, 2313; Synthesis, 1972, 397; Bull. Soc. Chiem., 1970, 2981). The radicals $R^3$ are substituted or unsubstituted alkyl, alkenyl, cycloalkyl, aryl or arylalkyl radicals having 1–20 carbon atoms, with compounds in which $R^3$ is the methyl or phenyl radical being particularly preferred according to the invention.

The reaction of the Grignard compounds with the cyclopent-2-en-1-ones substituted in the 3-position is preferably carried out in a molar ratio of 1:1 in a solvent comprising one or a mixture of ethers, preferably in diethyl ether, tert-butyl methyl ether or, in particular, tetrahydrofuran, at a temperature of from −20° to 120°, preferably from 0° to 70° C.

The cyclopentenone compound, if desired dissolved in ether, is preferably metered continuously or in portions into the ethereal solution of the Grignard compound and the reaction is continued for about another 1–3 hours after addition is complete.

After the reaction is complete, the magnesium alkoxide formed is hydrolyzed at room temperature by addition of preferably not more than a stoichiometric amount of water (with respect to the amount of Mg present). The hydrolysis and dehydration taking place in one step are finally completed at elevated temperatures of about 20°–100° C., preferably at about 70° C., for 1–3 hours. This step is preferably carried out in an inert, compatible solvent. Preferred solvents include ethers, such as diethyl ether, tert-butyl methyl ether, or tetrahydrofuran, or mixtures of one or more ethers, with one or both of hexane and/or heptane. In the latter case, it is preferred that the ratio by volume of all hexane and heptane pursuant to the ether(s) present is 1:1 to 4:1.

The magnesium salt which forms in the hydrolysis and dehydration step completely binds the water present in the reaction mixture, so that cooling to room temperature and removal of the precipitated magnesium salt gives a clear, solid-free and water-free solution which can be used directly for the reaction with a metallating agent, and the metallated product can then be reacted with a transition metal halide according to equation (C) to give the corresponding transition metal complex.

This reaction to form the transition metal complex can be carried out by generally known methods as are described, for example, in "Chemistry of organozirconium and -hafnium compounds", D. G. Cardin, M. F. Lappert, C. L. Raston; 1986, Ellis Horwood Limited; "Organometalllic Chemistry of Titanium, Zirconium, and Hafnium" 1974-Academic Press New York and London, P. C. Wailes, R. S. P. Coutts, H. Weigold; Gmelin-Handbuch der anorganischen Chemie-Supplement to 8th edition-Volumes 10 and 11, "Zirconium- und Hafnium organische Verbindungen", p. 26ff-Verlag Chemie, Weinheim-1973.

The invention is described further in the following examples, which are provided for purposes of description and are not intended to limit the scope of the invention.

EXAMPLE 1

Preparation of bis(1-methyl-3-octylcyclopentadienyl) dichloride 17.26 g (0.71 mol) of magnesium turnings were introduced into 30 ml of tetrahydrofuran (THF), and 2 g of octyl bromide was added to initiate the Grignard reaction. After the Grignard reaction had started, the remaining octyl bromide (total of 115.9 g; 0.6 mol) dissolved in 70 ml of THF was metered in such a way that gentle refluxing occurred.

After addition was complete, the mixture was allowed to react further for another 2 hours under reflux.

The mixture was then cooled to 0° C. and 3-methyl-2-cyclopenten-1-one (0.5 mol, 48.1 g), dissolved in 20 ml of THF and 80 ml of hexane, was added at this temperature.

After the metered addition, the mixture was allowed to react further for 3 h at room temperature (RT).

At RT, 170 ml of hexane and the stoichiometric amount of water necessary for the hydrolysis (0.6 mol, 10.8 g) were then added.

After addition was complete, the mixture was refluxed for another 2 hours, subsequently cooled to RT and the magnesium salt which formed was removed. The clear, solids-free filtrate was introduced first, and butyllithium (25 molar in hexane, 0.4 mol, 160 ml) was added at RT over a period of 30 minutes. The mixture was stirred further for 1 h at 50° C.

46.6 g of zirconium tetrachloride (0.2 mol) were then added at 0° C., the mixture was stirred for 1 hour at RT and for 2 hours under reflux.

The LiCl which precipitated was subsequently removed and the solvent was distilled off.

The remaining residue was recrystallized from hexane. This gave 77.4 g of product (yield: 71%)

Zr (calc.: 16.74) found: 16.9

Cl (calc.: 13.02) found: 13.3

$^1$H-NMR: (CDCl$_3$)

6.1–5.8 (m, 6 H, Cp); 2.6–2.38 (m,4H, —CH$_2$—); 2.2 (s, 6 H, —CH$_3$); 1.6–1.1 (m, 24 H, —(CH$_2$)$_6$—); 0.85 (t, 6 H, —CH$_3$)

EXAMPLE 2

Preparation of bis(1-i-butyl-3-methylcyclopentadienyl)zirconium dichloride

The procedure and starting materials were those of Example 1, except that 0.6 mol of i-butyl chloride was used in place of the octyl bromide. This gave 61.4 g of product (yield: 71%)

Zr (calc.: 21.1) found: 20.8

Cl (calc.: 16.4) found: 16.1

The $^1$H-NMR (CDCl$_3$) spectrum of the product is shown in FIG. 1.

EXAMPLE 3 a) Preparation of bis(1-n-butyl-3-methylcyclopentadienyl) zirconium dichloride

The procedure and starting materials were those of Example 1, except that 0.6 mol of n-butyl chloride was used in place of octyl bromide. This gave 67.5 g of product (yield: 78%)

Zr (calc.: 21.1) found: 20.7

Cl (calc.: 16.4) found: 16.1

$^1$H-NMR: (CDCl$_3$)

6.1–5.9 (m, 6 H, Cp); 2.65–2.38 (m, 4 H, —CH$_2$—); 2.2 (s, 6 H, —CH$_3$); 1.6–1.25 (m, 8 H, —CH$_2$CH$_2$—); 0.9 (t,6 H, —CH$_3$)

b) Preparation of bis (1-n-butyl-3-methylcyclopentadienyl) zirconium dichloride with isolation of the intermediate 1-n-butyl-3-methylcyclopentadiene 19.44 g of magnesium turnings (0.8 mol) were introduced into 40 ml of THF, and 1 g of n-butyl chloride was added to initiate the Grignard reaction.

After the Grignard reaction had started, a further 63.8 g of n-butyl chloride (total of 0.7 mol), dissolved in 150 ml of tetrahydrofuran, were added dropwise in such a way that gentle refluxing occurred.

After addition was complete, the mixture was reacted further for another 2 hours under reflux. It was then cooled to 0° C. and 67.3 g of 3-methyl-2-cyclopenten-1-one (0.7 mol), dissolved in 40 ml of tetrahydrofuran and 140 ml of hexane, were metered in.

The mixture was subsequently stirred at RT (room temperature) for another 2 hours. 200 ml of hexane were then added at RT and 12.6 g (0.7 mol) of H$_2$O were slowly metered in.

Figure 2:
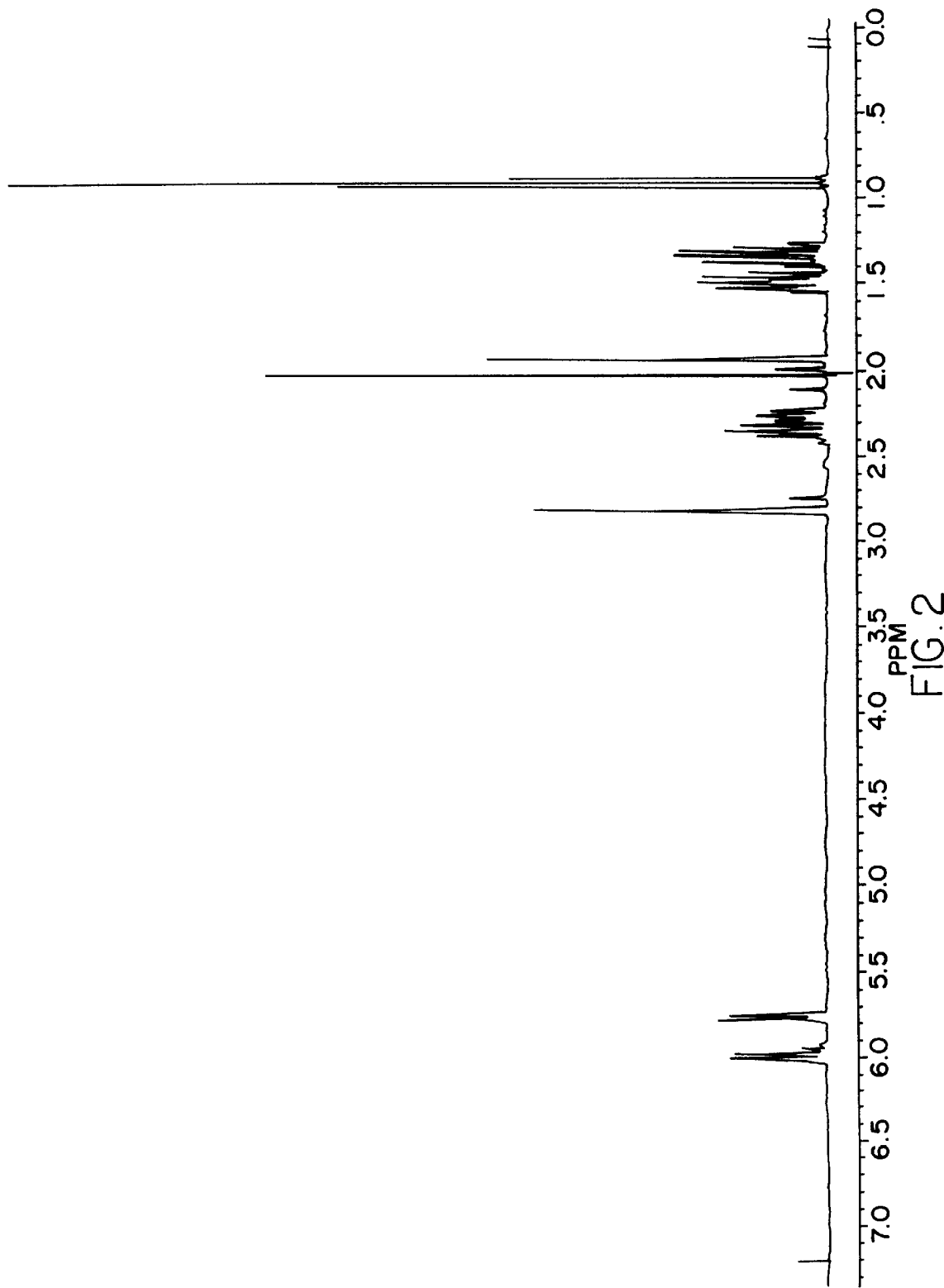

After the addition of the water, the mixture was refluxed for another 1 hour. After cooling to RT, the precipitated magnesium salts were removed and the filtrate was freed of solvent. The residue remaining after stripping off the solvent was examined by means of $^1$H-NMR. The spectrum, which is shown in FIG. 2, showed absolutely no remaining unde-hydrated alcohol, 1-n-butyl-3-methylcyclopent-2-en-1-ol. This result compares favorably to the results of reaction using n-butyllithium (Example 4, FIG. 3) in place of n-butyl-Grignard (this Example 3(b), FIG. 2).

The residue was then distilled at 45° C./mbar. This gave 85 g of distillate.

70 g of the distillate were introduced into 200 ml of pentane and 26 ml of tetrahydrofuran and, at RT, 146 ml of butyllithium (2.5 molar in hexane; 0.365 mol) were added dropwise. After addition of the butyllithium, the mixture was refluxed for another 30 min. 42.5 g (0.183 mol) of zirconium tetrachloride were introduced into the reaction mixture which had been cooled to 0° C. It was then refluxed for another 1 hour.

After cooling to RT, the precipitated LiCl was removed and the filtrate was cooled to −20° C. The precipitated product was filtered off and dried.

This gave 65.5 of product (83% of theory) whose $^1$H-NMR spectrum was identical to that in Example 3.a)

EXAMPLE 4

Comparative Example to 3.b): butyllithium used in place of Grignard 41.6 ml of butyllithium (2.5 molar in hexane; 104 mmol) were introduced first at −10° C.

Figure 3:
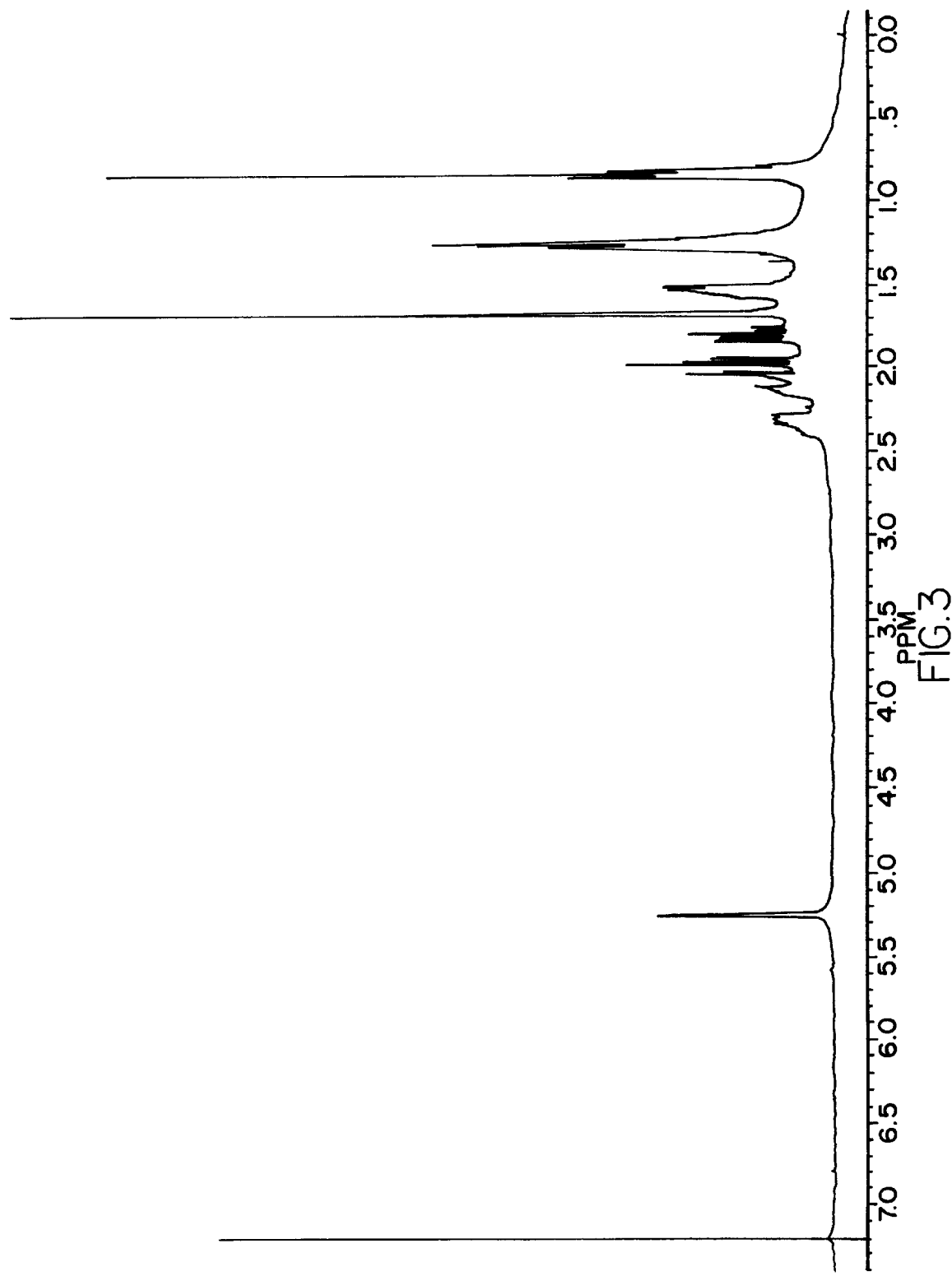

Over a period of 45 min, a mixture of 27 ml of hexane, 9 ml of THF and 10 g of 3-methyl-2-cyclopenten-1-one (0.104 mol) was added dropwise. After the addition was complete, the mixture was stirred for 4 h at RT. 1.87 g of water (0.104 mol) were then added dropwise, the mixture was stirred for 1 hour at RT and for 1 hour under reflux, cooled and filtered. The filtrate was freed of solvent and examined by means of $^1$H-NMR (CDCl$_3$); the spectrum is shown in FIG. 3. Only the pure alcohol 1-n-butyl-3-methylcyclopent-2-en-1-ol was detectable.

Dehydration had not occurred and thus 1-butyl-3-methylcyclopentadine had not been formed.

EXAMPLE 5

Preparation of bis(1-ethyl-3-methylcyclopentadienyl) zirconium dichloride

The procedure and starting materials were as in Example 1, except that 0.6 mol of ethyl bromide was used in place of octyl bromide. This gave 51.2 g of product (yield: 68%)

Zr (calc.: 24.23) found: 23.5

Cl (calc.: 18.83): found: 18.6

$^1$H-NMR: (CDCl$_3$):

6.1–5.9 (m, 6 H Cp); 2.72–2.49 (m, H,—CH$_2$—); 2.2 (s, 6 H, —CH$_3$): 1.15 (d, 6 H, —CH$_3$)

What is claimed is:

1. A process for preparing a 1,3-disubstituted cyclopentadienyl-transition metal complex, comprising in a first step, reacting a cyclopent-2-en-1-one substituted in the 3-position with a Grignard compound of the formula R$^2$MgX according to equation (A)

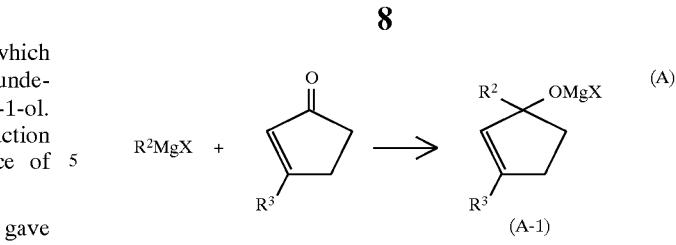

(A-1)

and hydrolyzing and dehydrating the alkoxide formed in equation (A) with not more than a stoichiometric amount of water, according to equation (B)

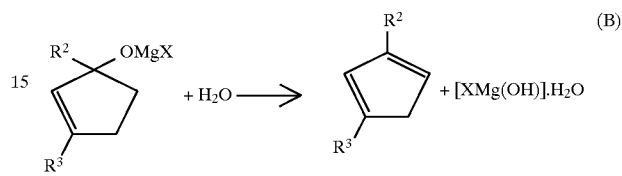

wherein each of R$^2$ and R$^3$ is independently of one another selected from the group consisting of C$_1$–C$_{20}$ substituted and unsubstituted alkyl, alkenyl, cycloalkyl, aryl, and arylalkyl radicals; and X is Cl, Br or I; and, in a second step, directly metallating the cyclopentadienyl product formed in equation (B), according to equation (C)

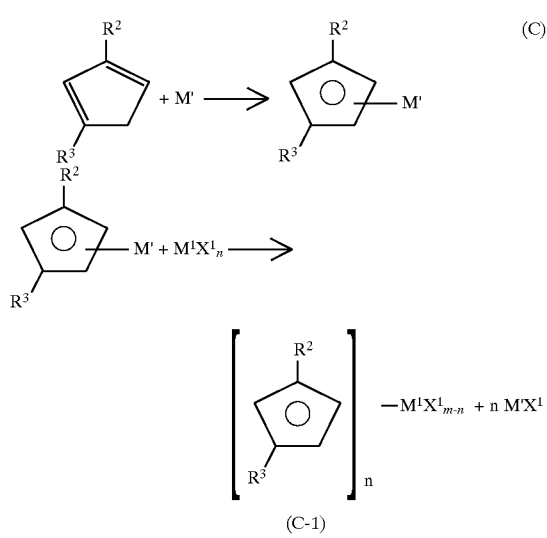

(C-1)

wherein

M' is metallating agent;

M$^1$ is Sc, Ti, Zr, Hf, Fe, V or Cr;

X$^1$ is Cl, Br or I;

m is the oxidation state of M$^1$; and n≦m;

and reacting the product (C-1) formed in equation (C) to form the corresponding complex of said product and said transition metal halide.

2. A process according to claim 1 wherein the metallating agent is Li, Na, K, NaH, KH or Li alkyl.

3. A process for preparing a 1,3-disubstituted cyclopentadienyl-transition metal complex according to claim 1, wherein in the Grignard compound R$^2$MgX, R$^2$ is an n-butyl, i-butyl or n-octyl radical.

4. A process for preparing a 1,3-disubstituted cyclopentadienyl-transition metal complex according to claim 1, wherein in the substituted cyclopent-2-en-1-one compound, R$^3$ is a methyl or phenyl radical.

5. A process for preparing a 1,3-disubstituted cyclopentadienyl-transition metal complex according to claim 1, wherein the Grignard compound $R^2MgX$ in equation (A) is used in tetrahydrofuran as solvent.

6. A process for preparing a 1,3-disubstituted cyclopentadienyl-transition metal complex according to claim 1, wherein the reaction (B) is carried out in a mixture of ether with one or both of hexane and heptane wherein the volume ratio of the total amount of hexane and heptane present to ether is 1:1 to 4:1.

7. A process for preparing a 1,3-disubstituted cyclopentadienyl-transition metal complex according to claim 1, wherein the cyclopentadiene derivative $CpR^2R^3$ obtained according to reaction (B) is isolated before further reaction thereof.

8. A process for preparing a 1,3-disubstituted cyclopentadienyl compound, comprising reacting a cyclopent-2-en-1-one substituted in the 3-position with a Grignard compound of the formula $R^2MgX$ according to equation (A)

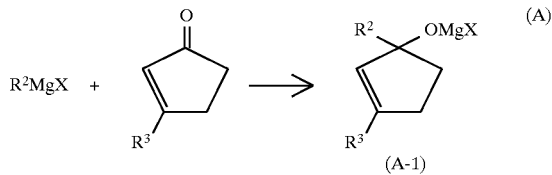

and hydrolyzing and dehydrating the alkoxide formed in equation (A) with not more than a stoichiometric amount of water, according to equation (B)

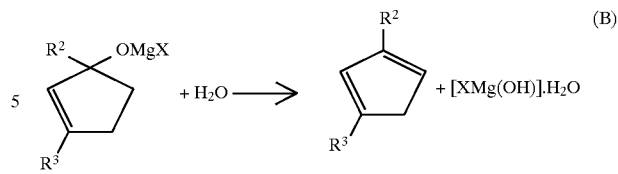

wherein each of $R^2$ and $R^3$ independently of one another is selected from the group consisting of $C_1$–$C_{20}$ substituted and unsubstituted alkyl, alkenyl, cycloalkyl, aryl, and arylalkyl radicals; and X is Cl, Br or I.

9. A process for preparing a 1,3-disubstituted cyclopentadienyl compound according to claim 8, wherein in the Grignard compound $R^2MgX$, $R^2$ is an n-butyl, i-butyl or n-octyl radical.

10. A process according to claim 8 wherein in the substituted cyclopent-2-en-1-one compound, $R^3$ is a methyl or phenyl radical.

11. A process for preparing a 1,3-disubstituted cyclopentadienyl compound according to claim 8, wherein the Grignard compound $R^2MgX$ in equation (A) is used in tetrahydrofuran as solvent.

\* \* \* \* \*